United States Patent [19]

Greenwood-Smith

[11] Patent Number: 4,551,848
[45] Date of Patent: Nov. 5, 1985

[54] LEAD-IN-AIR MONITOR

[75] Inventor: Robin Greenwood-Smith, Mount Isa, Australia

[73] Assignee: Mount Isa Mines Limited, Australia

[21] Appl. No.: 445,197

[22] Filed: Nov. 29, 1982

[30] Foreign Application Priority Data

Dec. 10, 1981 [AU] Australia ............... PF1904

[51] Int. Cl.⁴ ........................................... G01N 23/22
[52] U.S. Cl. ...................................... 378/045; 378/50
[58] Field of Search ............................. 378/44, 45, 50

[56] References Cited

U.S. PATENT DOCUMENTS

| | | | |
|---|---|---|---|
| 2,722,998 | 11/1955 | Hall | 73/28 |
| 3,984,679 | 10/1976 | Lublin et al. | 378/45 |
| 4,056,969 | 11/1977 | Barringer | 250/255 |
| 4,152,591 | 5/1979 | Averitt et al. | 378/47 |

FOREIGN PATENT DOCUMENTS 1060880 3/1967 United Kingdom ............... 73/28

Primary Examiner—Alfred E. Smith
Assistant Examiner—T. N. Grigsby
Attorney, Agent, or Firm—Darby & Darby

[57] ABSTRACT

The invention comprises a filtration unit which retains particles from air passed through a filter medium, a transport mechanism which moves the medium to a station where the particles are subjected to X-rays, apparatus responsive to X-ray fluorescence exited by the X-rays in a predetermined element, for example lead, during a predetermined time interval and issuing a count signal indicative of quantity of the element and a microprocessor for controlling the transport and counting apparatus.

12 Claims, 2 Drawing Figures

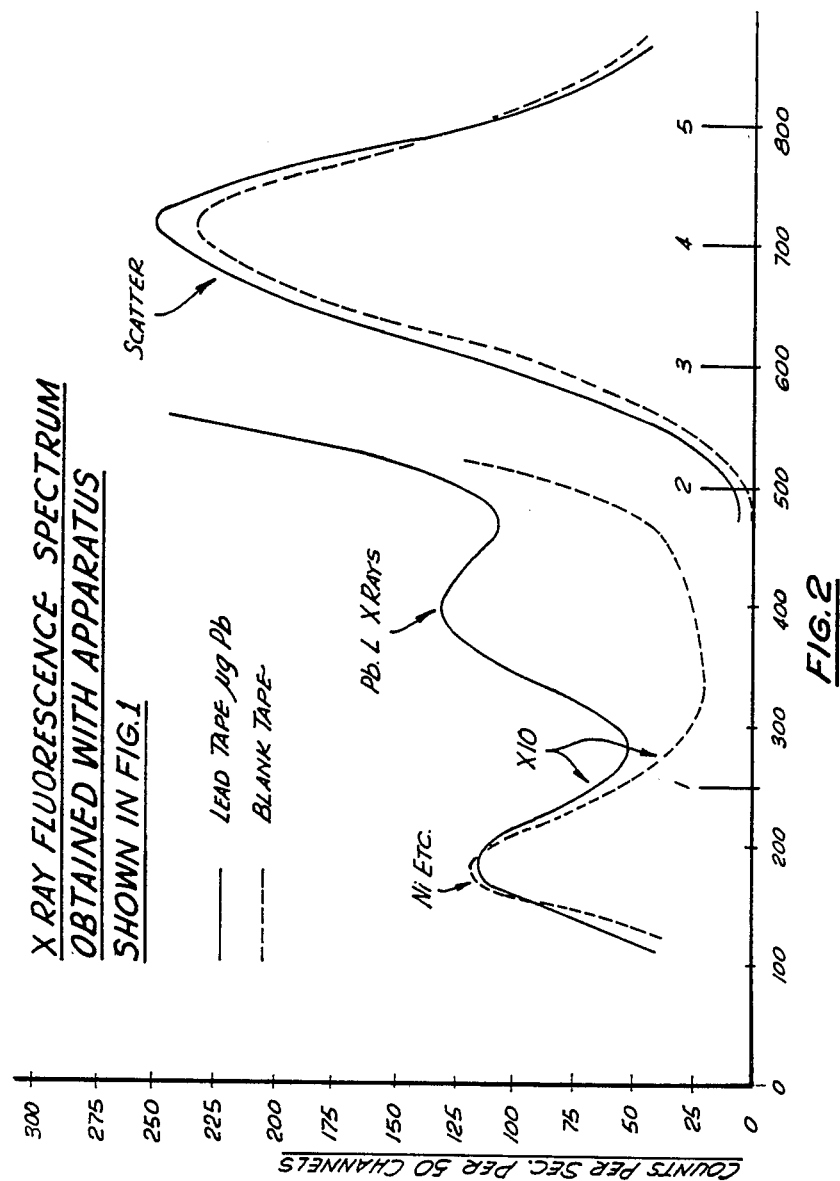

4,551,848

LEAD-IN-AIR MONITOR

FIELD OF THE INVENTION

This invention relates to a method and apparatus for monitoring air for the presence of lead. The invention is also applicable for monitoring the concentration of certain other elements in air.

DESCRIPTION OF THE PRIOR ART

Present standard of occupational health require a concentration of less than 150 ug/m$^3$ of lead in air at a work place.

To date there has not been available a satisfactory method for continuously and automatically monitoring the concentration of lead in air. Measurement has usually been conducted by filtering air samples during a period to retain particulate matter from the air, and then removing the filter media to a laboratory where the concentration of retained lead is measured.

SUMMARY OF THE INVENTION

According to a first aspect the present invention consists in apparatus for monitoring air comprising:

first means to filter a quantity of air and to retain on a filter media particles filtered therefrom at a first station, second means to transport the media and retained particles from the first station to a second station, third means to expose the particles at the second station to X-rays, fourth means responsive to X-ray fluorescence excited by the X-rays in a predetermined element, if any, present in the exposed particles during a predetermined interval and issuing a count signal indicative thereof, and a circuit including a microprocessor controlling the second and fourth means.

Preferred embodiments of the invention automatically and repetitively sample air from the environment, filter out particulate matter, irradiate the filtered matter with X-rays, count the X-ray fluorescence, and calculate the concentration of lead or another X-ray fluorescent element in the air having regard to sample and count conditions including source strength. The apparatus records data obtained and issues warnings if predetermined levels are exceeded.

BRIEF DESCRIPTION OF THE DRAWINGS

An embodiment of the invention will now be described by way of example only with reference to the accompanying drawings wherein:

FIG. 2 is a typical X-ray fluorescence spectrum of a sample containing 80 ug of lead in comparison with blank filter media, obtained by use of the apparatus of FIG. 1.

DESCRIPTION OF PREFERRED EMBODIMENT

Figure 1:
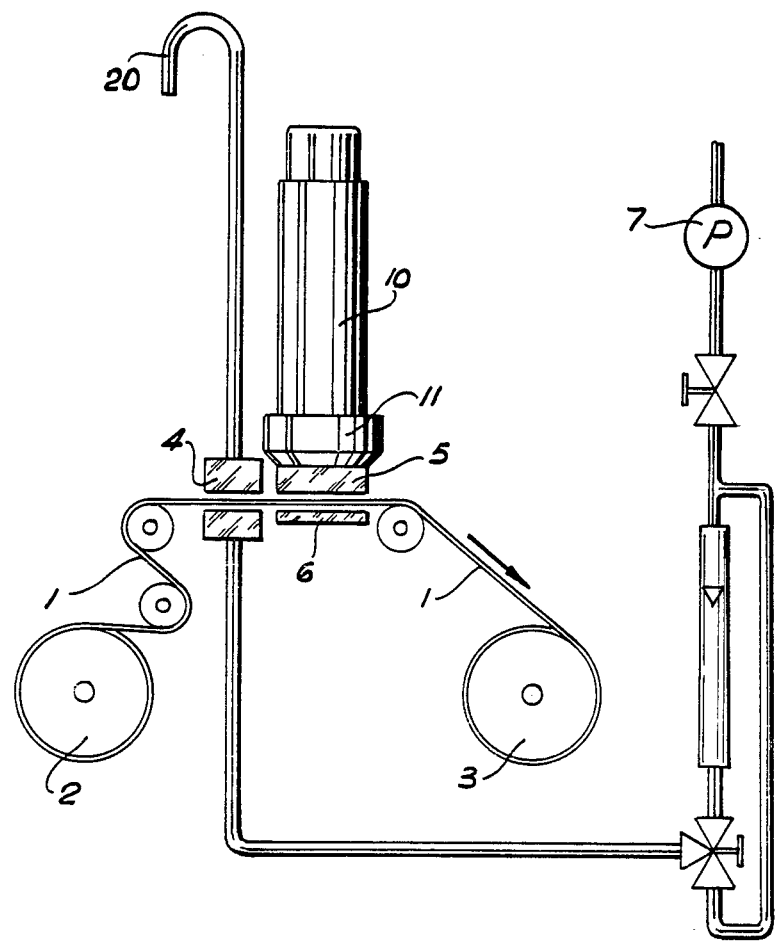
FIG. 1 is a schematic drawing of apparatus according to the invention.

With reference to FIG. 1 there is shown apparatus for monitoring the presence of lead in air and comprising filter media 1 in the form of length of tape supplied from a supply spool 2 from which it is to be unwound and extending to a take up spool 3 onto which it is to be wound.

A sample of air to be tested is conducted to filter station 4 and is passed through filter media 1, particulate matter in the air being in use retained on the filter.

In the present example the air to be tested is the environment of the apparatus and is drawn in at sampler 8 by pump 7. The air is pumped by pump 7 at a flow rate which is predetermined by flow control system 9.

Air is pumped by pump 7 at a predetermined flow rate, for example, 5 liters per minute from the environment for a predetermined sampling time interval, which may for example be ½ hour or 2 hours.

At the expiry of the sampling interval, the tape is advanced by a motor means so that the portion at filter station 4 arrives at analysis station 5 and fresh filter media is exposed at filter station 4. The tape is supported between station 4 and 5 by table 6.

The media from filter station 4 together with retained particulate matter is, at analysis station 5, exposed to X-rays in the present example from an overlying cadmium 109 source of about 10 millicuries.

The radioisotope is mounted in an analysis head 10. A scintillation crystal 11 is fitted behind the source with a thin stainless steel filter to act as a partial absorber of unwanted radiation. Fluoresence X-rays exacted in lead on the filter media, plus scattered X-rays, enter the scintillation detector, are detected and amplified by a photo multiplier and the pulses are further amplified electronically.

These pulses are interpreted by microprocessor means 12 which then act to control the spectral response of analysis head 10 so that peak response to scatter radiation is maintained at a predetermined value by adjusting the voltage applied to the photomultiiplier component of analysis head 10. Microprocesser 12 also controls the transport of filter media 1 from spool 2 to spool 3. A typical X-ray fluorescence spectrum from the scintillation detector is shown in FIG. 2. The spectrum contains two peaks one due to lead L X-rays and the other from scattering of incident X-rays. Electronic discriminators are set as shown in FIG. 2 with "scatter counts" being all counts between 2 and 6 and "lead counts" being all counts between 1 and 2.

An INTEL 8085 microprocessor is installed in the instrument and controls all of its operations. Its basic cycle is to control the timing of the sucking of air through the sample, the counting cycle, and calculating lead-in-air value for each sample on the filter tape.

The power supply for the microprocessor has been selected to be immune to large power mains variations. It is an inverter type power supply taking mains voltage, rectifying it to DC, passing it through an oscillator whose output is then rectified again to provide a second DC voltage totally isolated from the mains, and with good regulation.

The microprocessor components are PC board mounted and those boards are inserted onto a rack with the boards mounted with their surfaces vertical so that dust etc. will not settle onto them. The boards are locked into the frame so that they cannot vibrate free.

There are two means for communication with the microprocessor. Firstly, a key pad is mounted on the front panel of the instrument which allows access to all variables in the microprocessor memory and to certain control functions so that the motor drive etc. can be started and stopped by key pad actions. Secondly, there is access to the microprocessor via a remote printer unit which provides all actions obtainable on the key pad. Another option allows the system to be multiplexed onto a single communication line for communication with a remote station.

The microprocessor memory is split into two parts. EPROM containing the program, solid state RAM for data manipulation by the microprocessor. A segment of the RAM is operated from a battery backed power source for storage of long term constants which need to be changed for calibration or timing purposes. The battery has capacity for some months operation without mains power connection to the instrument. Access is available to all data in RAM via the key pad or terminal.

The microprocessor has full control over the photomultiplier high voltage with a D/A converter providing a reference signal for the high voltage power supply. Six further D/A converters adjust the levels of six pulse height discriminators which operate on the photomultiplier spectrum. Each of these discriminators feeds one of six counting registers which can be read, reset, started and stopped by the microprocessor.

The microprocessor cycle begins by advancing the paper tape by one unit to place fresh paper under the sample head and the previous sample under the analysis head. It then sucks air through the sample head for a preset time. Whilst doing this it also analyses the previous sample for a different preset time which is less than the sampling time. On the completion of the analysis time, the analyser calculates the lead-in-air based on an entered value of the air flow from the pump (for example 5 liters/minute). This result may be displayed on a displayed adjacent the key pad and may be printed out in a set format on the printer. In addition that data is entered into part of the PROM memory. Up to 50 previous values are stored in this memory, thus at any time a log of previous data for 50 samples can be accessed and inspected. This data can be accessed from the printer or remote computer. At the end of the sampling time the cycle begins again.

The operation of the system is totally automatic once the program has been put into normal mode. There is a test mode in which the time cycle is halted and allows inspection of data and also allows the possibility of scanning the analyser spectrum into the microprocessor to allow checking and fault finding. The microprocessor contains, in the program, an automatic gain control system which inspects the scatter X-ray section of the spectrum, and controls the instrument so that the scatter peak is centred at a preset voltage. Thus if for any reason the instrument's spectrum shifts it will be brought back into line very quickly. This obviates the need for continuous checking of the instrument as it compensates for any drift in the photomultiplier/electronics. It performs these adjustments by varying the photomultiplier high voltage to change its gain.

The instrument has provision for automatic insertion of a standard sample which is supported below the analyser table and can be rotated into the field of view of the analyser head. However, stability is quite satisfactory without need to use the automatic standardisation. If desired the microprocessor may store the date of supply and strength of the radioisotope source and can calculate the source strength on line at any time and correct the calculated amount of lead on the tape accordingly. The standardising disc also acts as an X-ray safety device—when the standardising disc is in, no X-rays may leave the bottom of the analyser head.

The ten millicurie source provides a small radiation hazard in the direct beam, however in normal operation, in which the hands might enter the beam for a few minutes, exposure is no problem. It is recommended that the standardising disc be raised during any potential exposure situations.

Although the invention is herein described primarily with reference to a monitor for lead in air, those skilled in the art will be able to modify the apparatus for monitoring arsenic and other X-ray fluorescent substances and such use is within the scope hereof.

I claim:

1. A health safeguard system for operation in an atmosphere containing hazardous substances such as lead, arsenic or other elements which are x-ray fluorescent wherein said system continuously suctions in air samples from said atmosphere and measures the level of these hazardous substances by bombarding them with x-ray excitaiton and measuring their fluorescence emission, which comprises:
   means for filtering a quantity of air and for retaining on a filter, media particles filtered therefrom at a first position;
   means for transporting the media and retained particles from the first position to a second position proximate to the first position;
   means for exposing the particles at the second position to X-rays;
   means for detecting radiation in a spectral range including the range of X-ray-induced fluorescence of predefined elements during a predetermimed interval, said detecting means including means for transmitting an output signal indicative of quantity of said radiation; and
   microprocessor means for controlling the transporting means and the detecting means so that the peak response to scatter radiation is maintained at a predetermined value.

2. An apparatus for monitoring air to protect the health of workers in an environment containing potentially dangerous levels of hazardous elements that fluoresce upon X-ray excitation, said apparatus comprising:
   means for filtering a quantity of air and for retaining, on filter media, particles filtered from the air at a first position;
   means for transporting the media containing said retained particles from the first position to a second position proximate to the first position;
   means for exposing the particles to X-ray radiation at the second position;
   means for detecting radiation in a spectral range including the range of X-ray induced fluorescence of predefined elements, said detecting means including means for generating an output signal indicative of the quantity of said radiation; and
   microprcessor means for controlling the transporting means and detecting means, said microprocessor means including automatic gain control means responsive to a portion of said output signal representing scatter radiation for contrlling the spectral response of said detecting means.

3. Apparatus according to claim 2 wherein the circuit includes first memory means for storage of a sequence of instruction controlling the sequence of operation of the first, second, third and fourth means, and second memory means for recording an issued count signal.

4. Apparatus as defined in claim 2 wherein the automatic gain control means maintains the peak response of said detecting means to scatter radiation at a preset value.

5. Apparatus according claim 2 wherein the fourth means includes a scintillation detector and means for discriminating between "scatter counts" and "elements counts".

6. Apparatus as defined in claim 5 wherein the microprocessor controls the instrument so that the peak response to the scatter X-ray radiation of the spectrum is always maintained at a preset value and wherein it measures the X-ray-induced fluorescence of lead-L and arsenic-K and background scatter radiation to determine the amount of toxic material on the filter tape, said regions of the spectrum being set by adjustable discriminators.

7. Apparatus according to claim 2 wherein the filter media is a tape which is periodically advanced so that an area thereof at the first station is conveyed to the second station.

8. Apparatus according to claim 7 wherein the predetermined element is lead and the third means comprises a cadmium 109 source.

9. Apparatus according to claim 8 wherein the detection means includes a scintillation detector and means for discriminating between "scatter counts" and "element counts."

10. Apparatus according to claim 9 wherein the circuit includes first memory means for storage of a sequence of instructions controlling the sequence of operation of the filtering, transporting, exposing and detecting means, and second memory means for recording an issued output signal.

11. Apparatus as defined in claim 10 wherein the automatic gain control means maintains the peak response of said detecting means to scatter radiation at a preset value.

12. Apparatus as defined in claim 10 wherein the microprocessor controls the instrument so that the peak response of the scatter X-ray radiaiton of the spectrum is always maintained at a preset value and wherein it measures the X-ray induced fluorescence of lead-L and arsenic-K and background scatter radiation to determine the amount of toxic material on the filter tape, the measurement of said regions of the spectrum controlled by adjustable discriminators.

* * * * *